US00PP33574P2

(12) United States Plant Patent
Bovio

(10) Patent No.: US PP33,574 P2
(45) Date of Patent: Oct. 19, 2021

(54) ***LAMIUM* PLANT NAMED 'ORCHID FROST GOLD'**

(50) Latin Name: *Lamium maculatum*
Varietal Denomination: Orchid Frost Gold

(71) Applicant: Michael Bovio, White Lake, MI (US)

(72) Inventor: Michael Bovio, White Lake, MI (US)

( * ) Notice: Subject to any disclaimer, the term of this patent is extended or adjusted under 35 U.S.C. 154(b) by 0 days.

(21) Appl. No.: 17/185,136

(22) Filed: Feb. 25, 2021

(51) Int. Cl.
*A01H 6/50* (2018.01)
*A01H 5/02* (2018.01)

(52) U.S. Cl.
USPC ..... Plt./444

(58) Field of Classification Search
USPC ..... Plt./444
See application file for complete search history.

*Primary Examiner* — Annette H Para
(74) *Attorney, Agent, or Firm* — Weatherly IP Solutions, LLC; James M. Weatherly

(57) ABSTRACT

A new cultivar of *Lamium* plant named 'Orchid Frost Gold' that is distinguishable by prostrate well-branched plant habit, leaves which are heart-shaped, dentate, lime-green in color, accented by a green edges, inflorescences of soft red-purple flowers which are held upright along the stems and above the prostrate foliage canopy, is disclosed.

2 Drawing Sheets

Genus and species: *Lamium maculatum.*
Variety denomination: 'Orchid Frost Gold'.

BACKGROUND

The present disclosure relates to a new and distinct cultivar of *Lamium* plant, also known as Dead Nettle or Spotted Dead Nettle, a perennial that is grown for use as an ornamental landscape and container plant. The new variety is known botanically as *Lamium maculatum* and will be referred to hereinafter by the cultivar name 'Orchid Frost Gold'.

The new *Lamium* variety 'Orchid Frost Gold' is a spontaneous whole plant mutation which arose during the chemical treatment of the inventor's variety *Lamium* 'Orchid Frost' (U.S. Plant Pat. No. 11,122). Specifically, Stage II tissue cultured microplants of 'Orchid Frost' were treated in the holding laboratory with a 0.001% solution of the chemical colchicine during February 2019 and observed after 6 months. The laboratory treatments resulted in a range of progeny including probable tetraploid mutations which would require further evaluation in vivo.

The chemical treatment of 'Orchid Frost' was intended to give rise to a tetraploid form of 'Orchid Frost' as disclosed in the co-pending application Ser. No. 17/185,218 *Lamium* Plant Named 'Orchid Frost Grande'. Although the present variety, 'Orchid Frost Gold', did not exhibit the characteristic vigor of a tetraploid variety, the inventor observed that its foliage and flowers are distinctly different from 'Orchid Frost' and that 'Orchid Frost Gold' was worthy of further trials.

In November 2019, unrooted cuttings of the single whole plant mutation 'Orchid Frost Gold' were transferred to a commercial nursery in Oxnard, Calif. where the plants were rooted and grown on, under the inventor's direction.

'Orchid Frost Gold' was first asexually propagated in January 2020 in a greenhouse in Oxnard, Calif. The inventor has confirmed that 'Orchid Frost Gold' is stable and reproduces true to type in successive generations of asexual reproduction.

SUMMARY

The following traits have been repeatedly observed and represent the distinguishing characteristics of 'Orchid Frost Gold'. 'Orchid Frost Gold' has not been tested under all possible conditions and phenotypic differences may be observed with variations in environmental, climatic, and cultural conditions, without however, any variance in genotype.

1. 'Orchid Frost Gold' exhibits a prostrate well-branched plant habit.
2. The leaves of 'Orchid Frost Gold' are heart-shaped, dentate, lime green in color, accented by mid green edges.
3. The inflorescences of 'Orchid Frost Gold' are held upright along the stems and above the prostrate foliage canopy.
4. The flowers of 'Orchid Frost Gold' are soft red-purple in color.
5. 'Orchid Frost Gold' grows and flowers rapidly. Flowering plants may be produced in 10 to 12 weeks from a cutting.

DESCRIPTION OF THE PHOTOGRAPHS

The accompanying color photographs illustrate the overall appearance of the new *Lamium* cultivar 'Orchid Frost Gold' showing the colors as true as it is reasonably possible to obtain in colored reproductions of this type. Photographs were taken in April 2019 in Oxnard, Calif. from a five months old plant grown outdoors in 3-gallon container, with one pinch after initial cutting establishment and without any chemical growth regulators. Colors in the photographs may differ from the color values cited in the detailed botanical description, which more accurately describes the actual colors of the new variety 'Orchid Frost Gold'.

DESCRIPTION OF THE NEW VARIETY

Figure 1:
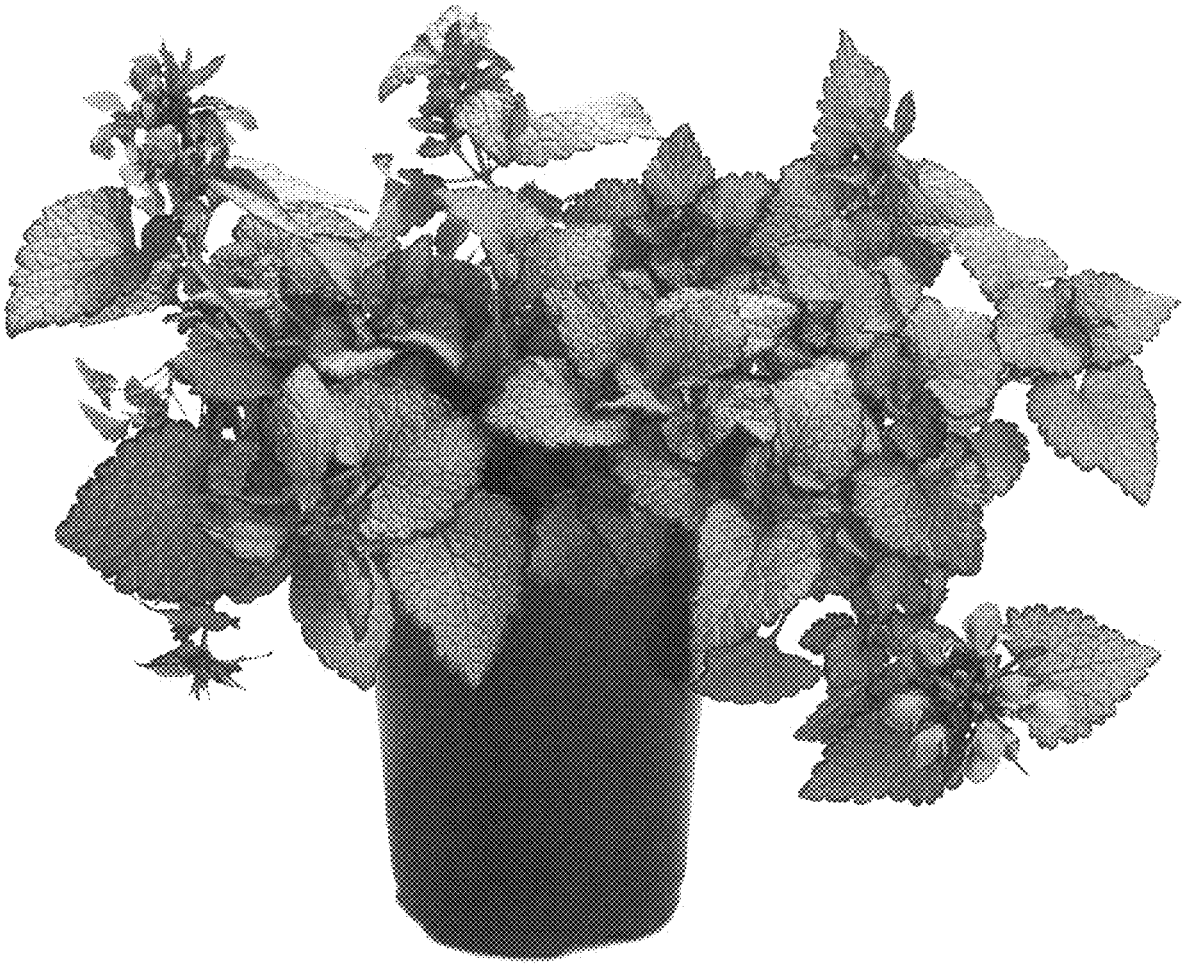
FIG. 1 depicts an entire plant 'Orchid Frost Gold' prior to flowering.
Figure 2:
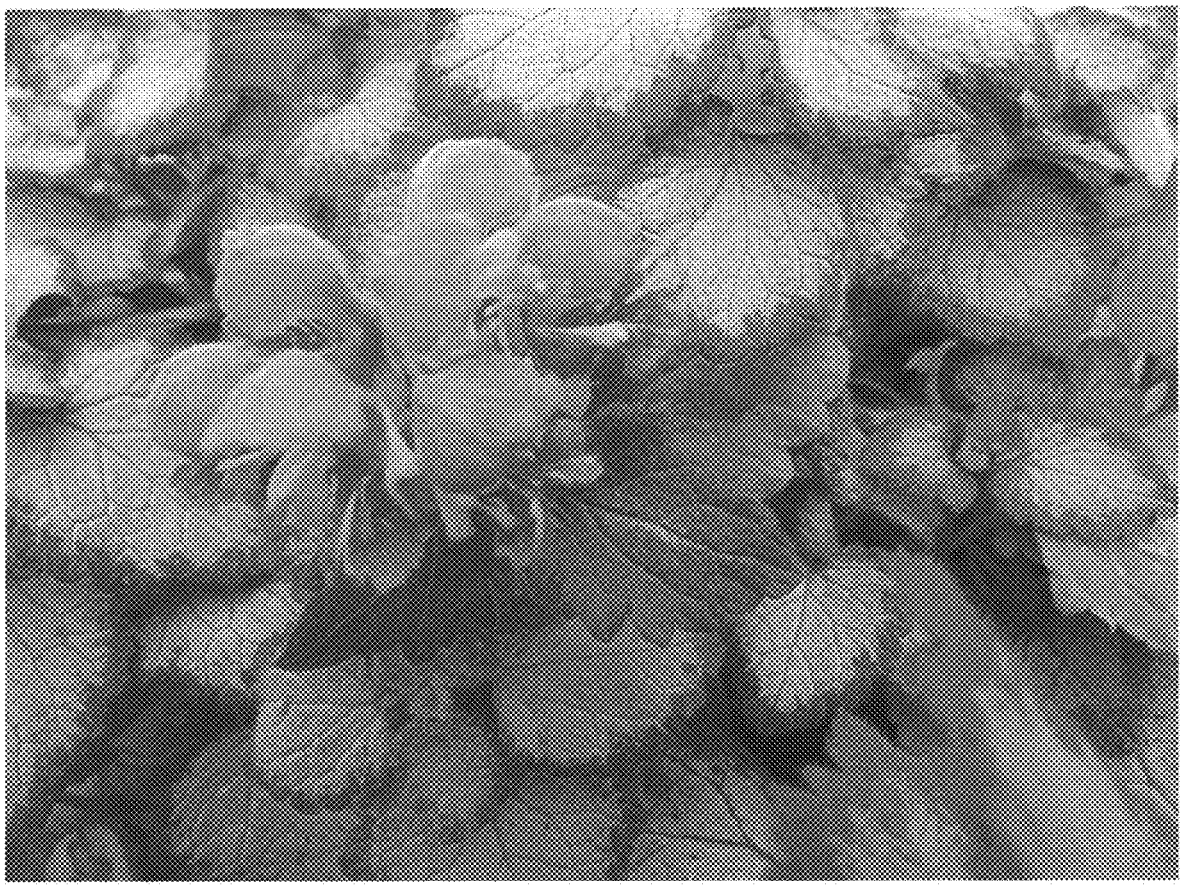
FIG. 2 depicts the inflorescence of 'Orchid Frost Gold'.

The following detailed descriptions set forth the distinctive characteristics of 'Orchid Frost Gold'. Observations, measurements, values, and comparisons were collected in April 2020 in Santa Barbara, Calif. from a five months old plant which had been growing outdoors in full sun in a 3 gallon container in Oxnard, Calif., with one pinch after initial cutting establishment and without any chemical growth regulators. Color determinations were made in accordance with The 2007 Royal Horticultural Society Colour Chart from London England, except where general color terms of ordinary dictionary significance are used.

Classification:

*Family.*—Lamiaceae.
*Genus.*—*Lamium.*
*Species.*—*maculatum.*
*Common name.*—Sage.

Parentage: 'Orchid Frost Gold' arose as a spontaneous whole plant mutation of the inventor's variety of *Lamium* plant named 'Orchid Frost'.

Plant:

*Propagation method.*—Softwood tip cuttings.
*Rooting system.*—Fine and fibrous.
*Vigor.*—Moderate vigor.
*Time to develop roots.*—5 days are needed for a cutting to develop roots at recommended rooting temperature of 20° to 22° Centigrade.
*Crop time.*—Approximately 12 weeks are required to produce a budded and flowering plant in a quart container from a rooted cutting.
*Suggested container sizes.*—Small cell or plug plants for mass planting or transplanting into larger containers or mixed containers. Larger containers up to 5 gallons are suitable for producing specimen plants for the garden and landscape.
*Use.*—Ornamental for use as a landscape plant or container plant.
*Type.*—Perennial.
*Overall dimensions.*—After 5 months growth, 15 cm in height, including the inflorescence, and 20 cm in width.
*Cultural requirements.*—Grow in full sun with moderate water and well-draining soil.
*Hardiness.*—USDA Zone 4.
*Form and growth habit.*—Predominantly dense prostrate foliage with inflorescences held above the foliage canopy.
*Blooming seasons.*—Spring, summer and fall.
*Lastingness of blooms.*—Inflorescence has some flower for 14 days, newly-opened individual flowers last for 2 to 3 days.

Branches:

*Quantity.*—8 to 12.
*Shape.*—Square.
*Length.*—20 cm measured to base of inflorescence.
*Width.*—3 to 4 mm towards the base tapering to 2 to 3 mm immediately below the inflorescence.
*Internode length.*—2 cm to 4 cm.
*Color.*—143C.
*Texture.*—Rough, pubescent, hairs fine, length up to 2 mm, color white NN155C.

Leaves:

*Type, arrangement.*—Simple, opposite.
*Attachment.*—Petiolate.
*Quantity per branch.*—5 to 7 pairs.
*Shape.*—Cordate.
*Length.*—45 mm.
*Width.*—43 mm.
*Margin.*—Dentate, 11 rounded teeth on each side edge, depth 2.0 to 2.5 mm, hairs fine, <0.5 mm in length, color NN155C.
*Venation.*—Pinnate, adaxial veins depressed, abaxial veins raised.
*Texture.*—Adaxial surface: Glabrous, glossy. Abaxial surface: Glabrescent.
*Variegation.*—Present on adaxial surface only.
*Leaf color* (*except for* 2 *to* 3 *non-variegated leaves immediately below inflorescence*)
*Adaxial surface.*—157C with green edge.
*Abaxial surface.*—143B, green edge absent.
*Leaf edge* (*adaxial surface only*).—Extends 3mm inwards from leaf margin, color 141B or 141C.
*Leaf color* (2 *to* 3 *leaves immediately below inflorescence*).—141B.
*Apex.*—Acute.
*Base.*—Cuneate.
*Fragrance.*—As wild nettles when rubbed.
*Stipules.*—Present in one or two pairs at each leaf axil. Small, petiolate cordate leaflets up to 2 cm in length and width. All other characteristics same as leaves (including variegation).

Petiole:

*Shape.*—Sulcate.
*Length.*—2.5 cm.
*Width.*—2 mm.
*Texture.*—Puberulent.
*Color.*—143C.

Inflorescence:

*Type.*—Verticillaster. Peduncle absent.
*Number of inflorescences per plant at maturity.*—20 to 25.
*Dimensions.*—5 cm in height and 4 cm in diameter.

Calyx:

*Position.*—Sessile.
*Shape.*—Campanulate, flared toward the apex.
*Length.*—6 mm to 9 mm.
*Width.*—7 mm across flared apex.

Sepals:

*Quantity.*—5, fused at base, otherwise free, divergent.
*Length.*—3 mm.
*Width.*—2.5 mm when flattened.
*Shape* (*where free*).—Narrow lanceoloate.
*Apex.*—Acuminate.
*Base.*—Truncate.
*Margin.*—Entire.
*Surface texture* (*both surfaces*).—Glabrous.
*Color.*—Adaxial surface (fused base): 144B. Adaxial surface (free sepals): 141B. Abaxial surface: 144B.

Flowers:

*Type.*—Zygomorphic, axillary, single, arranged in verticillasters.
*Quantity.*—20 to 25 per inflorescence.

*Shape.*—Corolla tube clavate, flowers present upper petal as a hemispherical hood and lower petals and lobes as lower lips.

*Fragrance.*—None observed except for secreted sweet-smelling nectar.

Bud:

*Shape.*—Globose.

*Diameter.*—4 mm to 5 mm.

*Texture.*—Densely pubescent, almost furry. Hairs very fine, white NN155C, 1 mm in length.

*Color.*—N78C.

Corolla:

*Shape.*—Tubular and curved upwards as tube emerges from calyx.

*Length.*—10 mm, including corolla tube, length 8 mm.

*Width* (*measured vertically*).—3 mm.

*Width* (*measured horizontally*).—2 mm.

*Texture* (*both surfaces*).—Glabrous, abaxial surface glandular and sticky with colorless nectar.

*Color* (*except tube, both surfaces*).—N78C.

*Color* (*corolla tube, both surfaces*).—NN155B, translucent.

Petals:

*Quantity.*—2.

*Arrangement.*—One upper petal (hood), one lower petal which appears as a prominent two-lobed lip facing downward and outward.

*Upper petal.*—Shape: Hooded, hemispherical. Width and height: 12 mm. Texture: Adaxial surface: Puberulent. Abaxial surface: Glabrous. Apex: Rounded. Base: Absent, upper petal, lower petals, corolla tube all fused. Margin: Smooth, wavy, lightly pubescent. Upper petal color (both surfaces): Ranges between N74C and N74D.

*Lower petal.*—Shape: Two adjacent rhomboid lobes, fused at base. Length (each lobe): 5 mm. Width (each lobe): 4 mm. Texture (both surfaces): Smooth, glabrous. Apex: Broad, undulating. Base: Truncate. Margin: Entire, gently undulating. Color (adaxial surfaces): N74C. Color (abaxial surface): N74C, N74D and 70D all individually present.

*Floral Bracts.*—Present as 1 or 2 claw-like bracts attached to margin above each of the lower petal lobes; 1.0 to 1.5 mm in length, 0.3 to 0.5 mm in width, color N78C.

Reproductive organs:

*Stamens.*—Quantity: 4. Filaments parallel, fused at base, length 15 to 17 mm, diameter 0.5 mm, color NN155D.

*Anther.*—Shape: Double ellipsoid, basally fused and attached to filament. Length: 2 mm. Width: 1 mm. Color: 187A.

*Pollen.*—Amount: Light. Color: N167B.

*Pistil.*—Quantity: 1 Style: length 15 to 17 mm, color NN155D (identical to filaments). Stigma: Forked (bifid), each fork 1.5 mm in length and slightly recurving.

*Ovary* (*only observed unfertilized*).—Position: Superior, appears as domed pinhead, 1.5 mm in diameter, color 196B.

Seed: None observed.

Disease and pest susceptibility: Susceptible to aphids (*Aphis gossypii*) and to deer and rabbit grazing. Generally outgrows most bacterial and viral infections.

Drought tolerance: Drought tolerant.

COMPARISON WITH PARENTAL LINE AND KNOWN VARIETY

In comparison with the parent variety 'Orchid Frost', which is also the closest variety known to the inventor, 'Orchid Frost Gold' exhibits soft red-purple flowers and lime green colored foliage, whereas plants of 'Orchid Frost' bear purple colored flowers and silver-grey colored foliage.

COMPARISON WITH CO-PENDING VARIETY

In comparison with the co-pending variety, 'Orchid Frost Grande', plants of 'Orchid Frost Gold' are less vigorous and exhibit leaves which are lime green in color with wide mid-green edges. The leaves of 'Orchid Frost Grande' are silver-white in color and exhibit narrower dark green edges. In addition, the flowers and buds of 'Orchid Frost Gold' are smaller and paler red-purple in color whereas the buds and flowers of 'Orchid Frost Grande' are larger and darker red-purple in color.

I claim:

1. A new and distinct variety of *Lamium* plant named 'Orchid Frost Gold' as described and illustrated herein.

* * * * *